Oct. 7, 1969 D. L. ARMSTRONG Plant Pat. 2,929
NECTARINE TREE
Filed Feb. 16, 1966
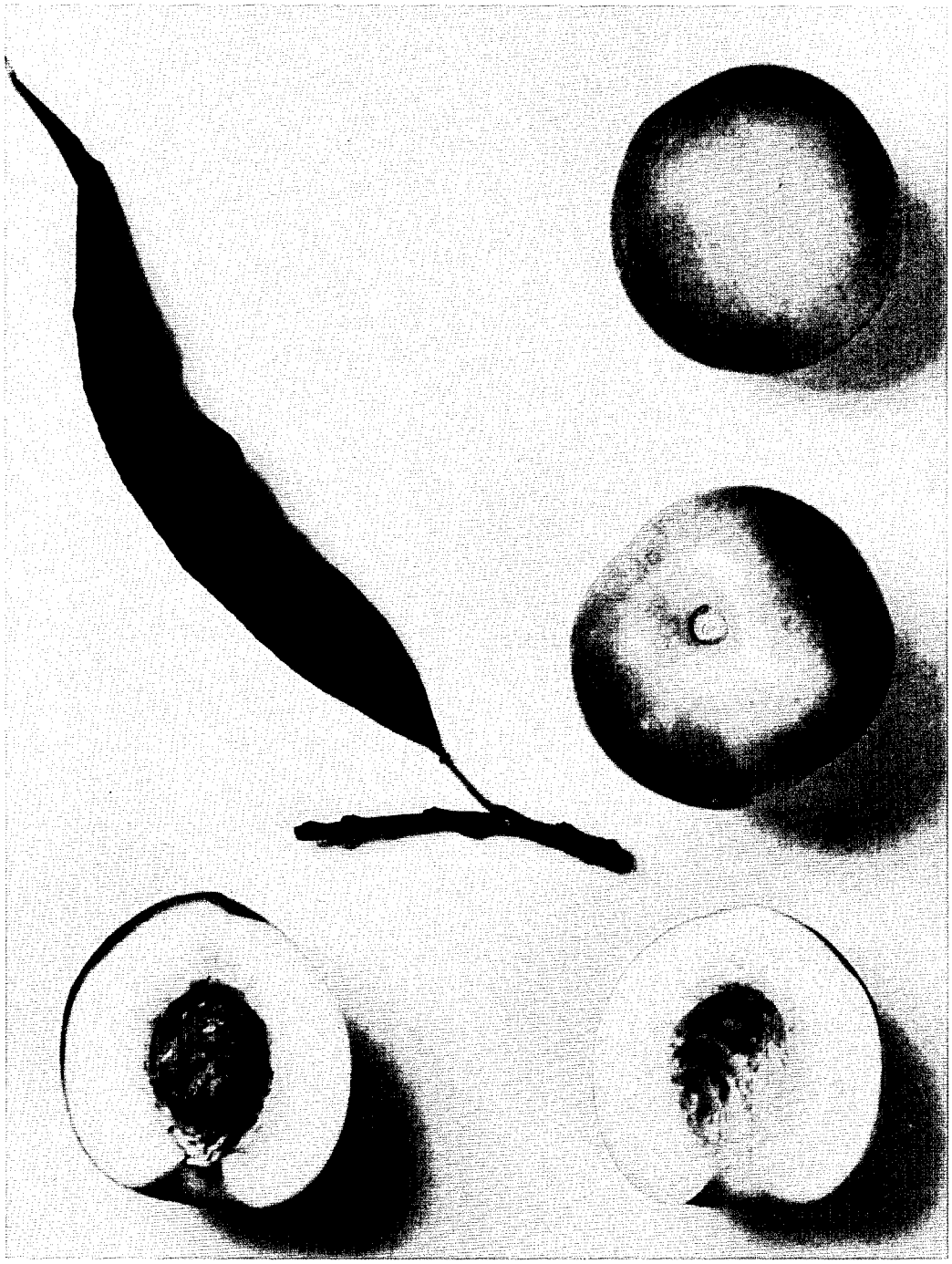
Inventor.
D. L. Armstrong
By: Robb & Robb
Attorneys.

United States Patent Office

Plant Pat. 2,929
Patented Oct. 7, 1969

2,929
NECTARINE TREE

David L. Armstrong, Ontario, Calif., assignor to Armstrong Nurseries, Inc., Ontario, Calif., a corporation of California Filed Feb. 16, 1968, Ser. No. 706,196
Int. Cl. A01h 5/08
U.S. Cl. Plt.—41 1 Claim The present invention relates to a new and distinct variety of nectarine tree which was originated by me as an open-pollinated seedling of an unnamed and unplanted dwarf nectarine variety which, in turn, was a seedling resulting from open-pollination of an unnamed and unpatented tall peach variety which was a seedling derived from cross-pollination of the nectarine variety known as "Pioneer" (Plant Patent No. 787), the seed parent, × an unnamed and unpatented dwarf peach resulting from an extended series of crosses going back two or three generations to the peach varieties known as "Babcock" (unpatented), "Double Pink" (unpatented), "Rio Oso Gem" (Plant Patent No. 84), "July Elberta" (Plant Patent No. 15), and "Chinese Dwarf" (unpatented, but identified as PI No. 41,395).

The general objective of this breeding was to produce a new and improved dwarf nectarine variety which bears attractive, yellow-fleshed, freestone fruit of good quality. This objective was fully achieved, along with other desirable features, as evidenced by the following unique combination of features which are outstanding in the new variety and which distinguish it from its parents, as well as from all other nectarine varieties of which I am aware:

(1) A vigorous, compact, bushy and dwarf tree habit having stem internodes averaging approximately ¼ inch in length, with leaves of relatively normal or larger size and appearance for peaches and nectarines, and thereby giving the tree an attractive, densely foliaged appearance, and attaining a height of about five to six feet in about ten years with little or no pruning;

(2) Showy, semi-double, pink flowers which give the tree a very attractive appearance when in bloom;

(3) A moderate chilling requirement, less than that of "Springtime" peach (Plant Patent No. 1,268) and about equal to that of "Tejon" peach (unpatented);

(4) Heavy fruit production;

(5) Small to medium sized, nearly round, yellow-fleshed, freestone fruit of good quality and flavor;

(6) Smooth fruit skin characteristic of the nectarine;

(7) A very attractive, bright red skin color ranging from near Jasper Red to near Oxblood Red, overlying a ground color ranging between Lemon Yellow and Indian Yellow; and (8) A fruit ripening period generally occurring in the second or third week of July at Wasco, Calif. and averaging from two to three weeks ahead of "Elberta" peach (unpatented) and a few days after "Halehaven" peach (unpatented).

The unnamed seed parent of my new nectarine variety was a dwarf nectarine variety similar to the new variety, but the fruit of this parent has less red skin coloring, more red color around the pit, the parent fruit ripens about ten days later than the fruit of the new variety, and the flowers of the parent variety are single, whereas those of the new variety are semi-double.

The new variety differs from its ancestor varieties mentioned by name in the foregoing by being a dwarf nectarine, whereas none of these varieties are dwarf nectarines. The varieties "Babcock," "Double Pink," "Rio Oso Gem," and "July Elberta" are all peach varieties of the tall type; "Pioneer" is a tall type nectarine variety; and "Chinese Dwarf" is a dwarf peach. Also, the fruit of the new variety has a bright red skin color, and is yellow-fleshed, freestone and July ripening, whereas "Chinese Dwarf" peach bears fruit which has pea green skin color, is white-fleshed, clingstone and is much later ripening.

In comparison with the dwarf nectarine variety known as "Golden Prolific" (Plant Patent No. 2,193), the fruit of the new variety has more red skin color and ripens in early mid-season, contrary to the relatively yellow skin color and late ripening of "Golden Prolific," and the new variety also has a much lower chilling requirement than "Golden Prolific."

As compared with the dwarf nectarine variety known as "Silver Prolific" (Plant Patent No. 2,325), the new variety differs therefrom in the same respects as described above in regard to the variety "Golden Prolific," and in addition, the fruit of the new variety is yellow-fleshed, whereas that of "Silver Prolific" is white-fleshed.

Asexual reproduction of my new variety by budding, as performed by me at Wasco, Calif., shows that the foregoing characteristics and distinctions come true to form and are established and transmitted through succeeding propagations.

The accompanying drawing shows typical specimens of the fruit and foliage of my new nectarine variety, with both exterior and sectional views of the fruit being shown, the latter exposing the stone in one half-section and the cavity in the other half-section, with all of the views being depicted in color as nearly true as it is reasonably possible to make the same in a color illustration of this character.

The following is a detailed description of my new variety, as based upon observation of specimens grown at Wasco, Calif., with color terminology in accordance with Robert F. Wilson's Horticultural Colour Chart (hereinafter abbreviated as (W)) and Ridgway's Color Standards and Nomenclature (hereinafter abbreviated as (R)), except where general color terms of ordinary dictionary significance are obvious:

TREE

Habit: Vigorous; upright-spreading; compact; bushy; dwarf; internodes of the stem average approximately ¼ inch in length; leaves are of relatively normal or larger size and appearance for peach varieties.

Chilling requirement: Moderate; less than that of "Springtime" peach and about equal to that of "Tejon" peach.

Fruit production: Bears heavy fruit crops in southern California.

Current growth:

*Surface texture.*—Smooth at first, with lenticels small and minute; some larger, cracked, slightly raised lenticels appear toward the base of the more vigorous shoots as they age.

*Color.*—Green or reddish on exposed surfaces at first, with lenticels appearing as small, near white dots, all becoming more brown with age.

Two-year wood:

*Surface texture.*—Somewhat bumpy and rough effect from raised nodes and buds and their closeness together on the stem; otherwise internodes generally smooth, with some slightly raised lenticels and irregular, longitudinal striations.

*Color.*—Brown, but sometimes reddish brown.

Old wood:

*Surface texture.*—With increasing diameter of the stem, the bumpiness and rough effect from the nodes and buds becomes less as they are covered by the growth of the stem, becoming more smooth over all, with moderate number of raised lenticels and some small, longitudinal fissures.

*Color.*—From grey to greyish-brown or reddish-brown on more exposed surfaces.

Leaves:

*Size.*—Usually from 6 inches to 9 inches long; from 1 inch to 1⅜ inches wide.

*Shape.*—Lanceolate, with apex acuminate.

*Color (mature).*—Upper surface—near Deep Dull Yellow-Green (1), Plate XXXII (R). Under surface—near Biscay Green, Plate XVII (R).

*Petiole.*—Medium length; medium thickness.

*Margin.*—Finely serrate; glandular.

*Glands.*—Mostly reniform; from small to medium size; usually 4 or 5, but sometimes 6 to 8 in number; borne both on the petiole and on the base of the blade.

Vegetative buds:

*Size.*—Small.

*Shape.*—Ovoid, unless compressed between flower buds.

*Scales.*—Pubescence thick; moderate length.

*Color.*—Dark brown.

FLOWERS

Dates first and full bloom: First bloom usually occurs at Wasco, Calif. from the last few days of February to the first few days of March, and full bloom usually occurs about the second week in March.

Dormant flower buds:

*Shape.*—Ovoid.

*Scales.*—Pubescent.

*Color.*—Dark brown, with pubescence giving a whitish effect.

Size (when fully open): Showy; medium size; about 1½ inches in diameter.

Petalage: Semi-double; usually from 10 to 12 petals; occasional single flowers.

Form: Cupped.

Color (open flower): Light pink.

FRUIT

Ripening dates: Generally ripens in the second or third week of July at Wasco, Calif.; ripens about two to three weeks ahead of "Elberta" peach and a few days after "Hale Haven" peach.

Maturity when described: Hard ripe.

Size: Variable, but generally medium size for nectarines.

*Axial diameter.*—From 2 inches to 2¼ inches.

*Transverse diameter in suture plane.*—From 1⅞ inches to 2¼ inches.

*Transverse diameter at right angles to suture plane.*—From 2⅛ inches to 2¼ inches.

Form: Relatively uniform; nearly symmetrical; from globose to broadly ovoid.

Suture: Generally shallow; extending from base to apex; sometimes extending over entire circumference; slight depression beyond pistil point.

Ventral surface: Rounded; usually slightly lipped throughout, and lips usually slightly unequal.

Stem cavity: Usualy rounded, but sometimes elongated in suture plane, with suture showing on one side.

*Depth.*—From ⅜ inch to ½ inch.

*Width.*—From ⅝ inch to ¾ inch.

Base: From rounded to truncate.

Apex: Usually rounded; pistil point insignificant and sometimes non-existent.

Stem: From medium to heavy caliper; glabrous; weak adherence to stone. Length—about ¼ inch.

Skin:

*Thickness.*—Thin.

*Texture.*—Medium.

*Tenacity to flesh.*—Free.

*Pubescence.*—None; characteristic smooth skin of the nectarine.

*Color.*—Ground color varies from near Lemon Yellow, Plate 4/2, page 4 (W) to near Indian Yellow, Plate 6/2, page 6 (W), heavily blushed with from near Jasper Red, Plate 018/2, page 107 (W) to near Oxblood Red, Plate 0023/1, page 191 (W).

Flesh:

*Quality.*—Medium firm; melting; fine texture.

*Aroma.*—Pronounced.

*Flavor.*—Good balance between sugar and acid; distinctive nectarine flavor.

*Color.*—Between Straw Yellow, Plate 604/2, page 67 (W) and Chinese Yellow, Plate 606/2, page 68 (W), with surface of pit cavity between Carmine Rose, Plate 621/1, page 75 (W) and Rose Madder, Plate 23/1, page 23 (W).

Stone:

*Tenacity of flesh.*—Free, but flesh adheres to stone slightly along both dorsel and ventral edges.

*Size.*—Medium; from about 1¼ inches to 1⅜ inches long; from about ⅞ inch to 1 inch wide; from about ¾ inch to ⅞ inch thick.

*Form.*—Ovoid; cuneate toward apex.

*Base.*—Oblique.

*Hilum.*—Oblong.

*Apex.*—Acute.

*Sides.*—Usually equal; curved on right and left sides; irregularly furrowed toward apex; pitted toward base.

*Ventral edge.*—Medium thickness; usually without wing toward base.

*Dorsal edge.*—From medium width to narrow; with shallow, narrow groove to above center; ridges on either side usually continuous.

*Color.*—Between Pecan Brown, Plate XXVIII (R) and Mikado Brown, Plate XXIX (R).

I claim:

1. A new and distinct variety of nectarine tree of the yellow-fleshed, freestone fruit-bearing and dwarf tree type, substantially as herein shown and described, characterized particularly as to novelty by the unique combination of a vigorous, compact, bushy, and dwarf tree habit having stem internodes averaging approximately ¼ inch in length, with leaves of relatively normal or larger size and appearance for peaches and nectarines, and thereby giving the tree an attractive, densely foliaged appearance, and attaining a height of about five to six feet in about ten years with little or no pruning, showy, semi-double, pink flowers which give the tree a very attractive appearance when in bloom, a moderate chilling requirement, less than that of "Springtime" peach (Plant Patent No. 1,268) and about equal to that of "Tejon" peach (unpatented), heavy fruit crop production, small to medium sized, nearly round, yellow-fleshed, freestone fruit of good quality and flavor, smooth fruit skin characteristic of the nectarine, a very attractive, bright red skin color ranging from near Jasper Red to near Oxblood Red, overlying a ground color ranging between Lemon Yellow and Indian Yellow, and a fruit ripening period generally occurring in the second or third week of July at Wasco, Calif., and averaging from two to three weeks ahead of "Elberta" peach (unpatented) and a few days after "Halehaven" peach (unpatented).

No references cited.

ROBERT E. BAGWILL, Primary Examiner